United States Patent [19]

Ericsson

[11] Patent Number: 4,854,627
[45] Date of Patent: Aug. 8, 1989

[54] METHOD AND A DEVICE FOR APPLYING OBJECTS ONTO A SURFACE

[75] Inventor: Magnus Ericsson, Stockholm, Sweden

[73] Assignee: AB Biodisk, Solno, Sweden

[21] Appl. No.: 87,647

[22] Filed: Aug. 19, 1987

[30] Foreign Application Priority Data

Aug. 28, 1986 [SE] Sweden .............................. 8603632

[51] Int. Cl.$^4$ .............................................. B66C 1/07
[52] U.S. Cl. .................................................. 294/64.1
[58] Field of Search ........................... 294/64.1, 65, 2; 269/21; 271/90, 91, 103; 279/3; 414/72, 121, 627, 737, 744 B, 752; 801/40

[56] References Cited

U.S. PATENT DOCUMENTS 3,721,352 3/1973 Messmer ............................ 294/64.1

FOREIGN PATENT DOCUMENTS 2001432 1/1979 United Kingdom .

Primary Examiner—James B. Marbert
Attorney, Agent, or Firm—Cushman, Darby & Cushman

[57] ABSTRACT

Figure 1:
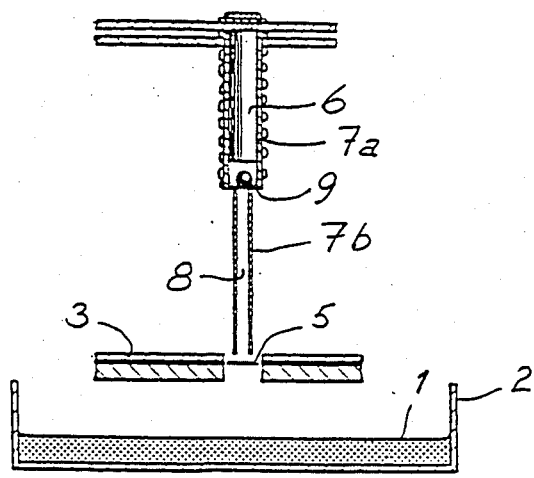

The invention relates to a method and a device for applying an object (5) such as an antibiotic patch onto a receiving surface (1) such as the surface of a culture. The object (5) is placed on a support (3) provided with holes (4) through which the objects are to be passed down to be applied to the receiving surface (1). According to the invention the objects (5) are retained by an applying means (6, 7) by means of a negative pressure during the transfer of the objects from the support (3) to the receiving surface (1), the applying means (6, 7) also generating the negative pressure during the transfer. (FIG. 1 is published).

7 Claims, 4 Drawing Sheets

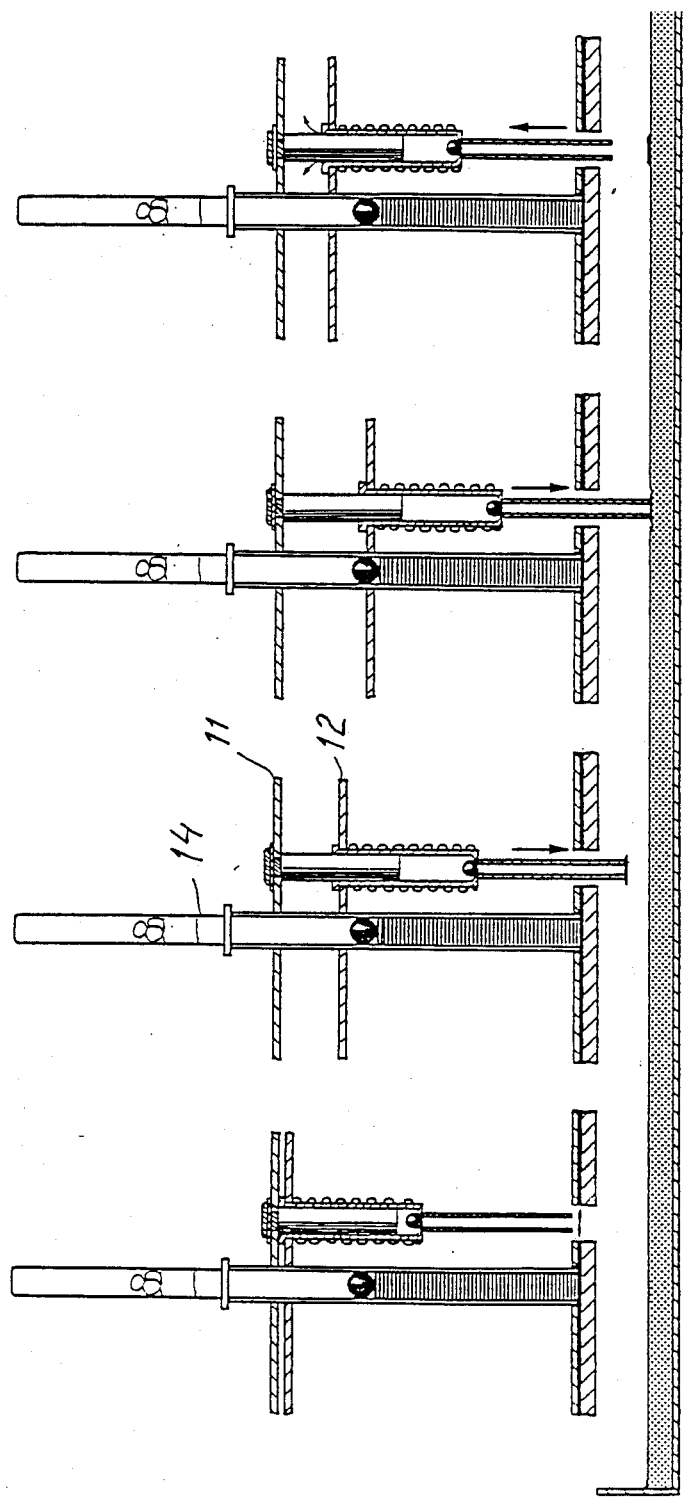

METHOD AND A DEVICE FOR APPLYING OBJECTS ONTO A SURFACE

This invention relates to a method and a device for applying objects onto a receiving surface, for example application of antibiotic patches onto an agar surface.

Several different devices for applying antibiotic patches onto an agar surface are previously known. In order to obtain correct test results the antibiotic patches must be passed down and pressed against the agar surface by means of a device so as to lie close to the agar surface. A known device of this type comprises a needle which is run through the object from a starting position after which the needle with the object is moved from a support to the receiving agar surface where an additional means is brought down around the needle and presses the antibiotic patch tightly against the agar surface. A disadvantage of this known device is that it will be complicated as it requires displacement of several parts in several different steps.

It is therefore the object of this invention to provide an improved method and an improved device for applying objects such as antibiotic patches onto a receiving surface such as an agar surface.

One characterizing feature of the invention is that objects such as antibiotic patches placed over holes in a support, which is placed above the receiving surface in a spaced relationship, are retained to the applying means by means of a negative pressure during the displacement of the object down through the hole in the support to the receiving surface.

Figure 2:
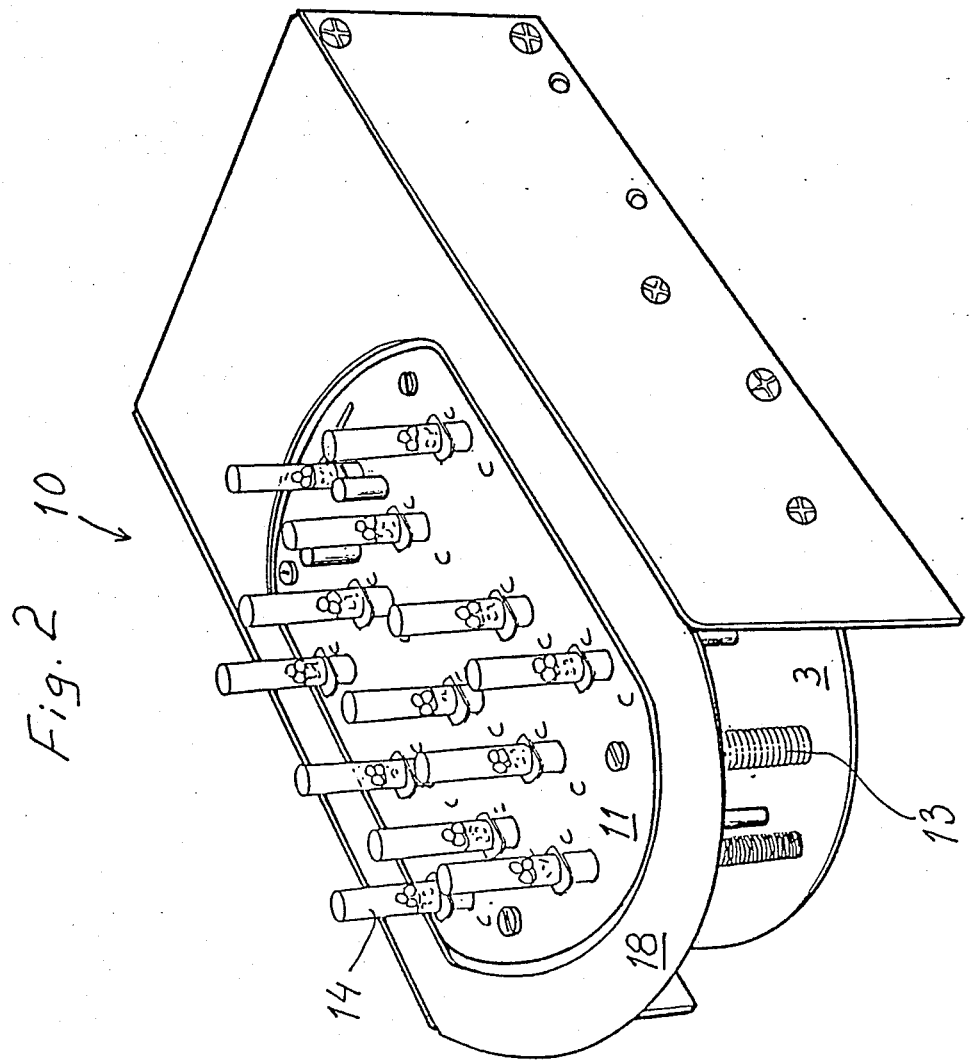
Figure 3:
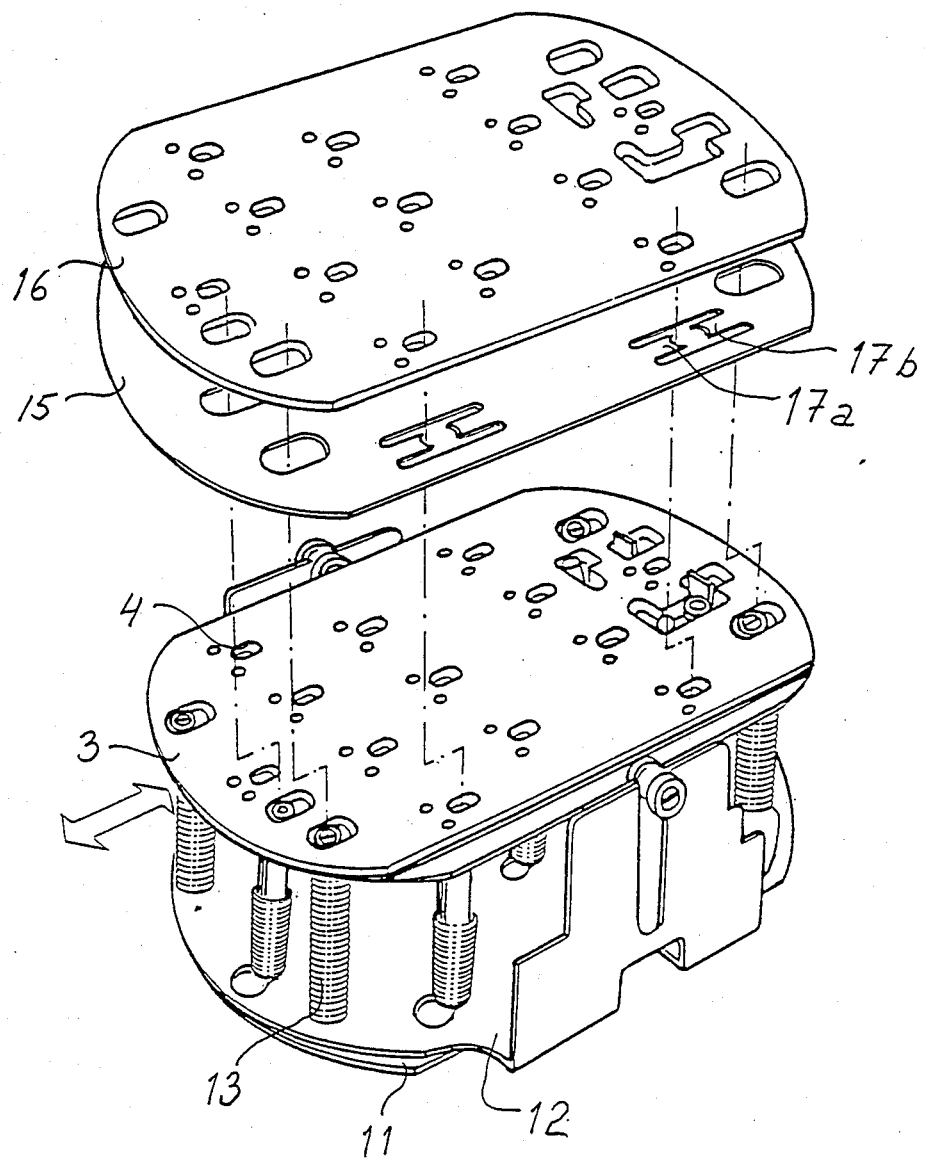

The invention is now described in greater detail in the form of a non-restrictive illustrative example shown on the accompanying drawings where FIG. 1 is a schematic section of an application device according to to the invention, FIG. 2 is a perspective view of an application device provided with application means according to the invention, FIG. 3 is a perspective view of part of the application device in FIG. 2 in an exploded view and shown as turned upside down, and FIG. 4A-D shows schematically application of an object onto an agar surface by means of an application means according to the invention in four different steps.

FIG. 1 shows a receiving surface 1 such as an agar surface in a Petri cup 2. Above this in a spaced relationship there is arranged a support 3 in which holes 4 are made. An object 5 such as an antibiotic patch which is to be applied to the receiving surface 1 is placed at the hole 4 on the support 3. An application means is placed above the hole 4 in the support 3 and, thus, above the object 5. This application means comprises a piston 6 attached to a stand not shown in FIG. 1 which piston extends downwards from the stand towards the support 3. The application means comprises further a tubular member 7 arranged concentrically with the piston 6 and internally lying close to the piston 6 in a substantially sealing relationship. This tubular member 7 is movable in the longitudinal direction of the piston and the tubular member by a drive means not shown in FIG. 1. The tubular member 7 is divided into an upper portion 7a and a lower portion 7b where the lower portion 7b is considerably narrower than the upper portion 7a. The lower tubular portion 7b has an outside diameter that is somewhat smaller than the diameter of the hole 4 in the support 3 so that the tubular member when being moved can be transferred down through the hole 4 in the support, the free lower portion of the tubular member 7 being brought down to the receiving surface 1.

When the tubular member 7 is moved down towards an object 5 placed above the hole 4 in the support 3 a closed space 8 will be formed between the object 5, the lower end of the piston 6 and the inner wall of the tubular member, when the lower part of the tubular member gets in contact with the object 5. In the further downward motion of the tubular member 7 the object 5 will be pressed through the hole 4 in the support 3 and simultaneously the volume of the closed space 8 will increase. As no air will enter this space the pressure therein will decrease below the surrounding atmospheric pressure and a negative pressure retaining the object 5 against the lower portion 7b of the tubular member will be created within the closed space 8. When the object 5 after passing the support 3 appears on the underside thereof and is no longer retained in the hole 4 the negative pressure within the closed space 8 is sufficient to retain the object during the further motion of the tubular member 7 downwards towards the receiving surface 1. The object is pressed against the agar surface 1 by means of the tubular member 7, adhesion forces appearing between the object 5 and the agar surface 1 which are sufficient to overcome the negative pressure within the closed space 8. When the volume of the closed space 8 does not increase any longer and a certain leakage of air occurs in the space 8 the negative pressure there will decrease so that the tubular member 7 can be retracted to the starting position without bringing along the object 5 from the agar surface again.

As shown in FIG. 1 a ball 9 is further arranged at the narrowing part of the tubular member 7 which ball provides a certain sealing effect between the lower portion 7b and the upper portion 7a in order to damp the return of the tubular member 7 after application of the object 5 onto the agar surface 1, which for instance can be achieved by means of springs, as shown in FIGS. 2 and 3.

Thus, a manually operated application device 10 is shown in FIG. 2 which is provided with the support 3 to which thirteen application means 6-8 are attached. The piston 6 of each application means is attached to the upper fixed plate 11 of the application device 10 while the movable tubular member 7 is attached to an upper movable plate 12 which can be lowered towards the support 3, springs 13 being clamped between the upper movable plate 12 and the support 3. Moreover, close to each application device a storage pipe 14 is arranged containing antibiotic patches to be applied. These storage pipes are of a type that is previously known and are therefore not explained here more in detail.

As is apparent from FIG. 3 two further plates are attached to the support 3, viz. a feeder plate 15 and a bottom plate 16. The function of the feeder plate 15 is to feed antibiotic patches 5 from the storage pipe 14 so that these get in a position straight in front of the hole in the support 3 and can be moved down through this by means of the application means, as described above. As is apparent from FIG. 3 the feeder plate 15 has feeding tongues 17a and 17b, one of which feeds the antibiotic patch to a position straight in front of the hole, while the other feeding tongue ensures the return of a possibly fed antibiotic patch to the storage pipe if no downward feeding of the antibiotic patch takes place through the thole 4. However what is not apparent from the figure, on both sides of the holes on its side facing the feeder plate 15 the bottom plate 16 is further provided with guide means between which the antibiotic patches are entered, which guide means also guide the feeder plate in its feeding by the aid of the slots on both sides of the feeding tongues 17a, 17b.

The application device shown in FIG. 2 is arranged, upon depression of the handle flap 18, first to feed an antibiotic patch from each of the storage pipes 14 by means of the feeder plate 15 to a position straight in front of each of the holes in order to press down there the tubular member 7 and consequently the antibiotic patch 5 through the hole 4 in the support 3, at continued depression of the handle flap, unti the antibiotic patch is pressed against the agar surface 1 when the depression of the handle flap is completed. The device will thereafter return to the original position by means of the springs 13. However, the return feeding is then damped a little by means of the ball 9 in the tubular member 7 which creates a counterpressure, the air only slowly leaking out along the walls between the upper tubular portion 7a and the piston 6, as indicated in FIG. 4D. The lateral surfaces of the handle flap 18 and in a direct contact with the upper movable plate 12 and move this downwards upon depression. As indicated in FIG. 3 the upper plate 12 is provided with a guide slot at its downwardly projecting edge portions which slot is guided against a projecting pin on the support 3. The application device 10 can also be provided with a push-out means not shown which after completed application of antibiotic patches onto the agar surface in a Petri cup located but not shown beneath the support 3 in FIG. 2 pushes off the Petri cup automatically. This push-out means can preferably also be formed so that it must be touched by a Petri cup to enable depression of the handle flap 18 and consequently the function of the whole application device.

Although not shown directly on the drawing the lower portion 7b of the tubular member can be formed with a very narrow inner cross section which, however, is extended at the lower free end so that the free end has a very slight wall thickness. Thus, the lower end of the lower tubular member is formed as a funnel turned upside down.

I claim:

1. A device for applying at least one object (5) such as an antibiotic patch onto a receiving surface (1) such as the surface of a culture, said device comprising a support (3) for the objects (5) to be applied, said support (3) being arranged above the receiving surface (1) in a placed relationship and holes (4) being made in said support (3) through which the objects can be passed down to the receiving surface (1), characterized in that at least one applying means (6, 7) is arranged to retain the object (5) by means of a negative pressure during the transfer from the support (3) to the receiving surface (1), said applying means (6, 7) also being arranged to generate the negative pressure during the transfer by way of a fixed interior piston (6) and a tubular member (7) movable in the longitudinal direction of the piston (6) and enclosing said piston, said piston internally lying close to the tubular member (7) in a substantially sealing relationship.

2. The device of claim 1, characterized in that the tubular member (7) has an upper portion (7a) enclosing the piston (6) and a lower portion (7b) with a smaller inside diameter than the upper portion (7a).

3. The device of claim 2, characterized in that a sealing means (9) is arranged at the transitional portion between the upper and the lower portions (7a, 7b) restricting the flow of air from the lower portion (7b) to the upper portion (7a).

4. The device of claim 2, characterized in that the lower portion (7b) has an extended inside diameter at its free end.

5. The device of claim 1, 2, or 3, characterized in that the holes (4) in the support (3) have substantially the same diameter as the objects (5).

6. The device of claim 1, 2 or 3, characterized in that several holes (4) are arranged in a pattern in the support (3) and that an applying means (6, 7) is arranged at each hole.

7. The device of claim 1, 2, or 3, characterized in that a drive means is arranged to move all tubular parts of the device together with the objects through the holes in the support for applying the objects onto the receiving surface.

* * * * *